United States Patent [19]

Clayman et al.

[11] Patent Number: 5,330,485
[45] Date of Patent: Jul. 19, 1994

[54] CEREBRAL INSTRUMENT GUIDE FRAME AND PROCEDURES UTILIZING IT

[76] Inventors: David A. Clayman; Tai Q. Nguyen, both of c/o University Medical Center, 655 W. 8th Ave., Jacksonville, Fla. 32209

[21] Appl. No.: 62,633

[22] Filed: May 18, 1993

Related U.S. Application Data

[63] Continuation-in-part of Ser. No. 786,278, Nov. 1, 1991.

[51] Int. Cl.$^5$ .............................................. A61B 17/00
[52] U.S. Cl. ............................................ 606/130; 606/1; 606/108
[58] Field of Search ............................ 606/130–108, 606/53, 54, 55, 56

[56]  References Cited

U.S. PATENT DOCUMENTS

| | | | |
|---|---|---|---|
| 3,053,256 | 9/1962 | Cooper et al. | 606/130 |
| 4,465,069 | 8/1984 | Barbier et al. | 606/130 |
| 4,592,352 | 6/1986 | Patil | 606/130 |
| 4,608,977 | 9/1986 | Brown | 606/130 |
| 4,638,798 | 1/1987 | Shielden et al. | 606/130 |
| 5,116,344 | 5/1992 | Sundquist | 606/130 |
| 5,201,742 | 4/1993 | Hasson | 606/130 |
| 5,246,448 | 9/1993 | Chang | 606/130 |
| 5,269,305 | 12/1993 | Corol | 606/130 X |

*Primary Examiner*—Peter A. Aschenbrenner
*Attorney, Agent, or Firm*—Nixon & Vanderhye

[57]  ABSTRACT

A cerebral instrument guide includes first and second arcs with aligned openings adjacent their ends, the openings defining a common axis about which the arcs are pivotal. The rods are mounted for movement along the common axis into contact with a human patient's auditory meati. A nasal bridge fixation element mounted on the first arc, as well as orbit pads, engage the bridge of a patient's nose, and his/her bony orbits. The appropriate angle to which the arcs should be pivoted with respect to each other is calculated by a computer program, as is the position to which a tubular instrument guide, slidable along the second arc and a projection from it intersecting the mid point of the common axis, is to be positioned to mark the burr hole on the patient's skull for performing a neurological procedure, such as a ventriculostomy. A needle is passed through the tubular instrument guide to mark the burr hole site. The cerebral instrument guide frame may be left in place, or removed, while a stereotactic instrument placement guide is used (after the burr hole is formed) to properly position the neurological instrument (e.g. catheter) used to perform the neurological procedure.

15 Claims, 5 Drawing Sheets

CEREBRAL INSTRUMENT GUIDE FRAME AND PROCEDURES UTILIZING IT

This application is a continuation-in-part of application Ser. No. 07/786,278 filed Nov. 1, 1991.

BACKGROUND AND SUMMARY OF THE INVENTION

There are many neurological procedures which require the accurate placement of a neurological instrument, including for biopsy, radioactive seed placement, and lesion generation. One of the most common neurological procedures requiring accurate placement is a ventriculostomy procedure in which a cerebral ventricle drain or shunt is installed. Such a drain or shunt is utilized for ventricular drainage when a patient manifests hydrocephalus resulting from congenital brain malformations, acute or chronic infections, tumors, intraventricular hemorrhage, or normal pressure hydrocephalus.

Conventional procedures for the placement of ventricular drains or shunts rely heavily on the skill of the neurosurgeon, and/or are relatively expensive and time consuming. After a CT scan, or other imaging, the neurosurgeon forms a burr hole in the skull, and then the neurosurgeon guides a catheter through the burr hole toward landmarks on the opposite side of the patient's head. It is necessary that the neurosurgeon be able to completely accurately visualize the internal tomography of the brain when performing this procedure, and it is presumed that the catheter is properly located when the surgeon obtains fluid returned through the catheter. In some circumstances, the neurosurgeon feels it advisable to check the location of the catheter, and for that purpose the patient must be subjected to another CT scan of the brain in order to verify proper location of the catheter. Since each separate, individual, CT scan is expensive, and since the prior art procedures are time consuming both for the neurosurgeon and the anaesthesiologist, there has long been a need for procedures more regularly and inexpensively accurately placing ventricular drain or shunt catheters, which will result in longer shunt patency and decreased morbidity due to shunt malposition.

According to one aspect of the invention of the parent application, a stereotactic neurological instrument placement guide is provided that may be utilized in numerous different types of neurological procedures, and which has ideal suitability for use in ventriculostomy procedures. The guide according to the invention is simple to construct and to utilize, and can readily enhance accuracy, reduce time, increase confidence, and reduce cost for a given level of confidence, in ventriculostomy procedures and other neurological treatment methods.

The stereotactic guide of the parent application has only first and second skull engaging point members, which have a common central axis. A frame mounts the skull engaging point members for controlled movement with respect to each other along the central axis. Means are provided defining a linear guide passage in the first point member, a straight line extension of the linear guide passage extending along a common central axis, and the linear guide passage is large enough for the passage of a neurological instrument (e.g. catheter or shunt) through it. The termination of the first point member coaxial with the linear passageway and common central axis provides for stabilizing the first point member in a burr hole; for example the termination may comprise a truncated cone.

The point members may be attached to arms, which in turn are attached to a guide sleeve and a guide element (bar or rod) which are movable with respect to each other. A locking screw can lock them in a position to which they have been moved, or they may be biased toward each other by an elastic band, spring loading, or the like. The means defining a linear passage may comprise a slotted sleeve rigidly fixed to the frame arm, with a slotted tubular element received within the sleeve and rotatable from one position in which the slots of the sleeve and tubular member are not aligned, to a second position in which the slots are aligned. When the slots are not aligned, the guide passage is closed and provides positive guiding of the catheter therethrough. When the slots are aligned, the placement guide may be removed from contact with the patient's skull, and the catheter.

According to the parent application, the key to proper utilization of the stereotactic neurological instrument placement guide is the proper location of the fixing point on the opposite side of the patient's skull from the burr hole. The positive location of the fixing point, which will receive the second point member of the placement guide, opposite the proposed site for the burr hole is determined utilizing a CT scan, magnetic resonance imaging (MRI), or another type of coordinate multiplanar tomographic imaging of the patient's skull. Utilizing X, Y, and Z coordinates for the burr hole (marked by a nipple marker or the like), and determining the coordinates of the particular portion of the ventricle, or other location within the brain, desired to be acted upon by the neurosurgeon, the data from the imaging can be used to calculate the loci of points along a straight line between the burr hole and the target area, which loci can be extended to the patient's skull on the opposite side thereof from the burr hole, and that part of the patient's skull can be marked with a nipple marker, oil, or the like. The calculations are preferably provided by vector parameterization, utilizing a programmable scientific calculator, and the gantry angle of the imaging equipment can be automatically accommodated.

Desirably the distance of the target point from the burr hole is also calculated according to the invention, so that the neurosurgeon can use indicia on the catheter to determine when the catheter has been inserted the distance necessary to properly position it at the target. Practicing the method according to the invention, since the placement of the fixing point is accurately determined, there is no necessity for a second CT scan, or the like.

While the invention will be described herein primarily with respect to ventriculostomy procedures, it is to be understood that both the apparatus and procedures according to the invention may be applied to a wide variety of neurological practices. In fact, the basic positioning facilitating features of the parent application are applicable not just to neurosurgery, but in general to determining the position of a line between two points on or within a human patient's body utilizing data normally determined from a coordinate multiplanar tomographic imaging (CT, MRI, etc.) of the patient's body during which the patient is disposed at an angle, and is incrementally advanced between images. Utilizing the present invention it is possible to practice procedures not heretofore contemplated, or to maximize the accuracy of present procedures, since according to the invention it is possible to accurately locate and determine the coordinates of two or more points on or within a human body (e.g. within the brain).

Also according to the present invention, the utility of the stereotactic neurological instrument placement guide described above is improved by utilization of a cerebral instrument guide frame and supporting computer programs. The cerebral instrument guide frame, and related procedures, according to the invention allow the neurosurgeon to mark the burr hole site and fixing point on the patient in the operating suite prior to applying the stereotactic instrument guide described above. This eliminates the need to mark these sites on the patient in the multiplanar tomographic imaging (CT scanning) suite. In this way it is possible to avoid accidental erasure or movement of identifying marks or markers placed by the radiologist. Further, instead of having a mark on the scalp, the neurosurgeon can directly mark the patient's skull, improving accuracy of the stereotactic instrument guide described above.

The cerebral instrument guide frame according to the present invention is preferably mounted in the patient's ears and on the bridge of the patient's nose. In addition to allowing—in association with the computer programs described hereafter—accurate location of the burr hole and fixing point, the cerebral instrument guide frame can serve as a fixing point for the stereotactic instrument guide described earlier. The cerebral instrument guide frame according to the invention thus provides a neurosurgeon a simple stereotactic method for catheter placement, or for other neurological procedures, and expands the utility of the stereotactic instrument guide described above.

A cerebral instrument guide frame for use with a live human patient according to the present invention comprises the following elements: A first arcuate member having first and second ends, and a radius. A second arcuate member having first and second ends and a radius, (the radius of the second arcuate member being greater than the radius of the first arcuate member). Aligned first and second openings provided adjacent each of the first and second ends of each of the first and second arcuate members. First and second rigid ear fixator rods mounted in the aligned openings, the first in the openings adjacent the first ends of the first and second arcuate members, and the second in the openings adjacent the second ends of the first and second arcuate members, the rods mounted for movement with respect to the first and second arcuate members along a common axis passing through the openings, and the arcuate members mounted for pivotal movement with respect to each other about the common axis. An abutment mounted on one of the arcuate members for engaging a portion of a patient's head to preclude movement of the arcuate member past that portion of the patient's head. And an instrument guide mounted on the other of the arcuate members for guiding an instrument aligned therewith into contact with the patient's head, the guide directed to the midpoint of the common axis.

The abutment preferably comprises a nasal bridge fixation element for engaging the bridge of a patient's nose, and the instrument guide comprises a tubular element mounted to one of the arcuate elements for movement with respect to that element along the arcuate extent thereof. The abutment is mounted on the first arcuate element and the instrument guide on the second arcuate element. A pair of orbit pads also may be mounted on the first arcuate element on opposite sides of the nasal bridge fixation element for engaging the patient's orbits. The tubular instrument guide element has an internal diameter slightly greater than the external diameter of a needle. The first and second arcuate members each preferably comprise a hemicircle, or semicircle, and the nasal bridge fixation element is mounted for radial movement with respect to the first arcuate element (that is, along the radius thereof). The first and second arcuate members preferably are made of aluminum, a rigid durable sterilizable medical-grade structural plastic, or the like.

The cerebral instrument guide frame according to the invention may be used in combination with the stereotactic neurological instrument placement guide as described above, with one of the point members of the skull engaging elements of the stereotactic neurological instrument guide engaging the tubular instrument guide element, and in alignment therewith. When the guide frame according to the present invention is combined with the stereotactic neurological instrument placement guide described above, typically the second point member comprises the "one of the point members", and the first and second arcuate members make an angle of about 160°-180° with respect to each other with the second point member in alignment with the tubular instrument guide element.

According to another aspect of the present invention, a cerebral instrument guide for use with a live human patient is provided which comprises the following elements: A first frame element having first and second ends, and a central portion. A nasal bridge fixation mounted on the first frame element at the central portion, and movable with respect to the first frame element. A second frame element having first and second ends, and a central portion. Pivot means for mounting the first and second frame elements for pivotal movement with respect to each other about a common axis. An instrument guide mounted on the second frame element, and movable with respect thereto and directed toward the midpoint of the common axis. And means for positively locating the pivot means with respect to the patient's head so that the axis remains stationary with respect to a predetermined portion of the patient's head.

Typically, the pivot means and the positively locating means comprise first and second ear fixation rods adapted to be inserted into the patient's ears and received within aligned openings in the first and second ends of the first and second frame elements. The rods may be slidable with respect to the frame elements to move toward and away from the patient's ears. The frame elements preferably comprise first and second hemicircles with the second frame element hemicircle having a larger radius than the first element hemicircle. The ear rods preferably have some covers—where they engage the patient's ears—of a soft material, such as soft rubber, to allow seating of the rod ends into the external auditory meatia.

The computer program utilized with the present invention accepts data from computed tomographic images representing five separate points: a target point in a cerebral ventricle, a point representing the intended burr hole site on the skull, a point at the right external auditory meatus, a point at the left external auditory meatus, and a point representing the interior superior edge of either bony orbit. The program corrects for CT scanner gantry tilt and then calculates an angle at which to separate and set the first and second arcs of the cerebral instrument guide frame, and an angle between a line containing the midpoint of the line in space (the common axis of the arcuate members) and the skull point, and a line in space connecting the ends of the arcs. The sliding instrument guide mounted on the second arcuate member is set at this calculated angle, and directed toward the skull.

When the apparatus described above is utilized, the patient first has a CT scan (or other multiplanar tomographic imaging) of the brain and skull. Neither the cerebral instrument guide frame nor the stereotactic instrument guide is mounted on the patient's head during the acquisition of the CT data, but following the CT scan procedure, the target, burr hole, right and left auditory meatia, and orbital ridge points are entered into the computer program to calculate the angles necessary. In the operating room, with or without the patient under general anesthesia, the cerebral instrument guide frame is then applied to the patient's head by symmetrically advancing the rods connecting the arc centrally toward and into the external ear canals, and then by seating the mid-line U-shaped nasal bridge onto the nasion. The angle between the first and second arcuate members and the position of sliding guide along the first arc are set, and the neurosurgeon can then pass a long needle down the sliding guide through the scalp and onto the skull at the skull point where a distinguishing mark for the burr hole can be made, and later for the fixing point. The cerebral instrument guide frame may then be removed and the stereotactic instrument guide used as a described above, or the cerebral instrument guide frame can be left in placed and repositioned to accept the fixing point of the stereotactic instrument guide.

According to another aspect of the present invention, a method of positively locating a burr hole site on a patient's skull during a neurological procedure on a human patient, using a guide comprising first and second frame members mounted for pivotal movement with respect to each other about a common axis defined by ear fixators, one of the frame members having a nasal bridge fixation, and the other having an instrument guide, is provided. The method comprises the steps of: (a) Effecting coordinate multiplanar tomographic imaging of the patient's head. (b) During the practice of step (a) determining locations of the target in the patient's head, the burr hole site on the patient's skull, the patient's left and rights auditory medati, and at least one of the patient's orbital ridges. (c) With a computer, calculating from the data determined in step (b) the angular positions of the frame members of the guide to mark the burr hole site and fixing point on the patient's skull, and the proper position of the instrument guide along the second frame member. Then (d) moving the ear fixations of the guide into positive contact with the patient's ears, and the nasal bridge fixation into positive contact with the patient's nasal bridge. And (e) moving the second frame member of the guide frame with respect to the first frame member to have the proper orientation to mark the burr hole site, and moving the instrument guide to the proper position along the second frame member, and then marking the burr hole site using the instrument guide.

The method can also be for positively locating a fixing point on the patient's skull in which case there is the further step of (f) moving the second frame member of the guide with respect to the first frame member to have the proper orientation to mark the fixing point on the patient's skull, and then marking the fixing point site using the instrument guide. Also, there may be the still further step, with the guide in place with the relative positions of the components as provided in step (f), of moving a stereotactic neurological placement guide having end point members into operative association with the burr hole site and the instrument guide on the second frame member; effecting formation of a burr hole; and passing an instrument through one of said stereotactic neurological placement guide point members engaging said burr hole, to pass the instrument to the target within the patient's skull.

Alternatively, the guide is removed from the patient's ears and nose, a burr hole is formed at the burr hole site, and the end point members of a stereotactic neurological placement guide having end point members is moved into operative association with the burr hole site and a fixing site opposite the burr hole site on the patient's skull. The neurlogical instrument is inserted through the burr hole and placement guide into operative association with the target within the patient's skull.

Step (c) may be practiced in part by using vector parameterization, and step (a) is practiced using a non-zero angle of inclination between imaging equipment and the patient while there is an incremental advance between images, the computations in step (c) taking into account the angle of inclination and the increment of advance between images.

In general, the invention facilitates and provides a method of performing a neurological procedure on a human patient utilizing a scanner, a cerebral instrument guide frame, and an operating room, that is greatly simplified with respect to the prior art, allowing the scanning to be done without a frame on the patient's head, and avoiding the expense and time delay of moving a patient from the operating room back to the scanner, and running a second scan on the patient with a frame attached to the patient's head. This aspect of the method of the invention comprises the steps of substantially sequentially: (a) Effecting coordinate multiplanar tomographic imaging of the patient's head with the scanner while the patient's head is free of frame attachments, to obtain data necessary for performing a neurological procedure. (b) Moving the patient to the operating room. (c) In the operating room, utilizing the data from step (a), fixing the cerebral instrument guide frame on the patient's head; and (d) substantially immediately after step (c), in the operating room, without transporting the patient back to the scanner to effect a second imaging, performing the neurological procedure on the patient, utilizing the cerebral instrument guide frame to guide one or more medical instruments (e. g. catheter, light pipe, laser, etc.).

It is a primary object of the present invention to provide an accurate, effective, and simplified manner of performing neurlogical procedures on a human patient. This and other objects of the invention will become clear from an inspection of the detailed description of the invention and from the appended claims.

DETAILED DESCRIPTION OF THE DRAWINGS

Figure 1:
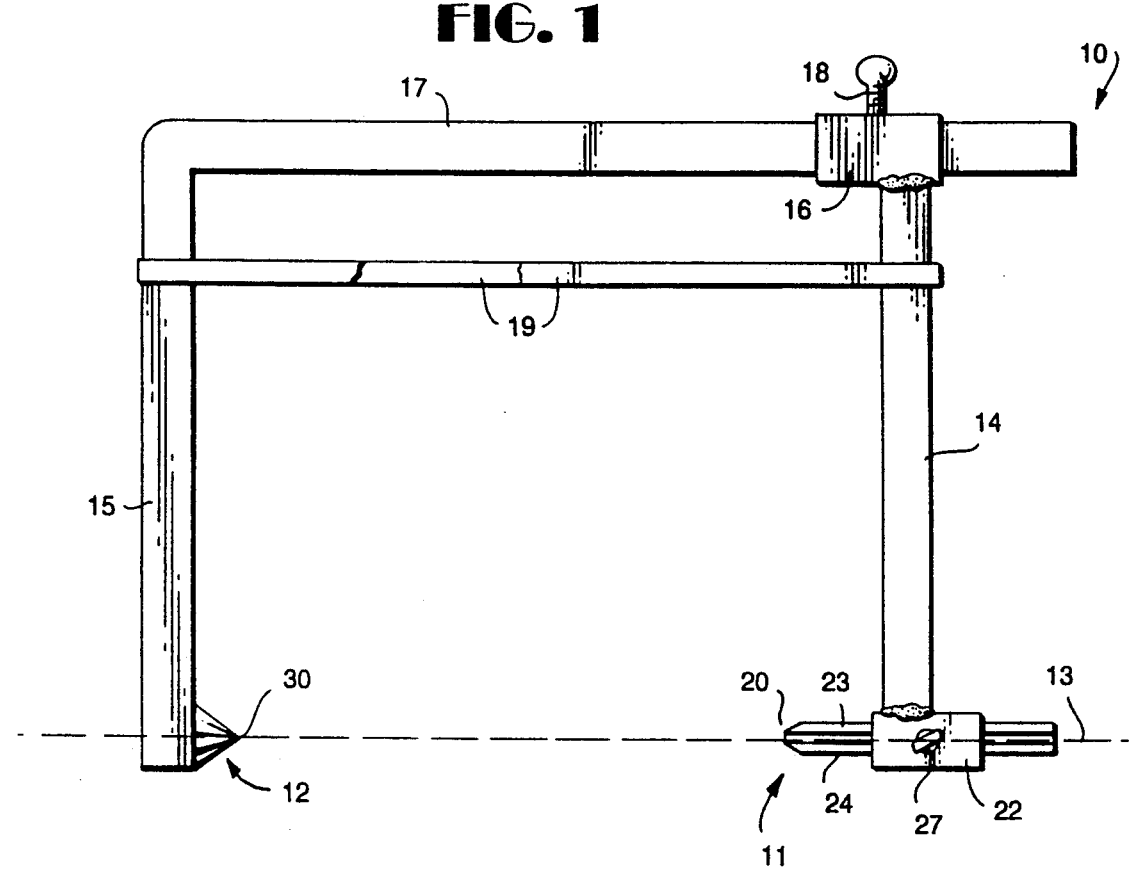
FIG. 1 is a side view of an exemplary stereotactic neurological instrument placement guide according to the invention.
Figure 5:
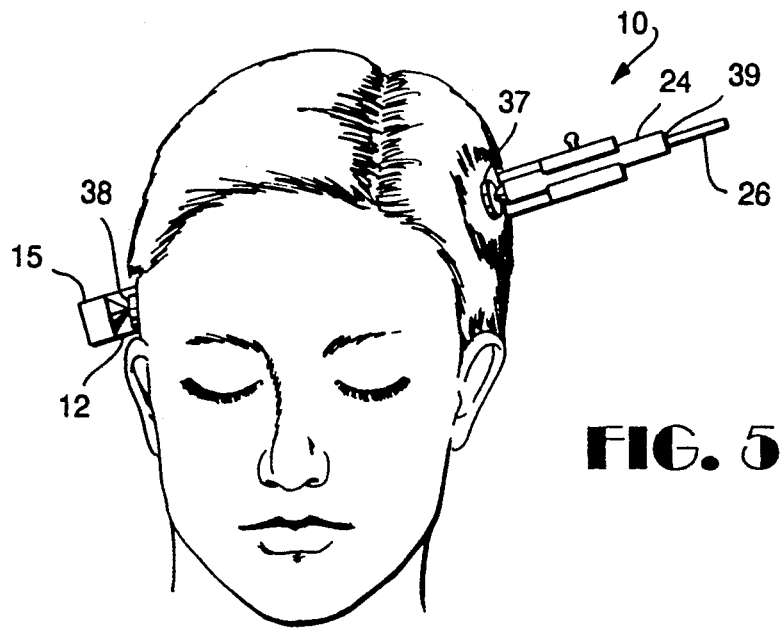
FIG. 5 is a schematic view showing the stereotactic neurological instrument placement guide of FIG. 1 in use on a patient's head with a catheter having been placed by the stereotactic neurological instrument placement guide.

FIGS. 1 and 5 illustrate an exemplary stereotactic neurological instrument placement guide according to the invention, shown generally at reference numeral 10. The guide 10 preferably is made of lightweight, rigid material, such as aluminum, titanium, hard plastic, or the like. It includes only two skull engaging elements, that is the skull engaging elements consist of a first skull engaging point member shown generally by reference numeral 11, and a second skull engaging point member shown generally by reference numeral 12. A frame mounts the members 11, 12 for movement toward and away from each other along a common central axis, preferably so that they move linearly with respect to each other along the linear axis 13. The frame preferably comprises a first arm 14, which preferably is rigidly connected to the first point member 11, and a second arm 15 which preferably is rigidly connected to the second point member 12. Movement of the arms 14, 15 with respect to each other, with the members 11, 12 along the axis 13, is preferably provided by a sleeve 16 rigidly attached to the first arm 14, and a guide element, such as a rod or bar, 17 rigidly connected to the second arm 15. The portions 15, 17 can be formed integrally (as by molding), as can the portions 14, 16.

In most circumstances, it is desirable to either be able to lock the frame of the device 10 so that the members 11, 12 are positioned at a specific distance from each other (corresponding to the dimension of the patient's skull at the operative area of use), or means are provided for biasing the arms 14, 15 toward each other, or for biasing the first member 11 toward the second member 12. Where locking is desired, a thumbscrew 18 may be provided threaded through an opening in the guide sleeve 16 and releasably engaging the guide element 17. When the guide element 17 is tightly engaged, relative movement between the arms 14, 15 is not possible, but when the thumbscrew 18 is loosened relative movement in a dimension parallel to the axis 13 is possible. Instead of, or in conjunction with, the thumb locking screw 18, an elastic band 19 may be provided, which exerts a force pulling the arms 14, 15 toward each other. Alternatively (not shown) a spring loading can be provided for the first point member 11 itself, the spring loading operating between the arm 14 and the end, skull engaging, termination 20 of the member 11, so that it is biased into contact with the patient's skull.

It is very desirable to be able to remove the guide 10 from contact with the patient's skull, and from contact with the neurological instrument (e.g. catheter), once the stereotactic device 10 has been utilized to properly guide the neurological instrument into place. This may be accomplished by the means most clearly illustrated in FIG. 2.

Figure 2:
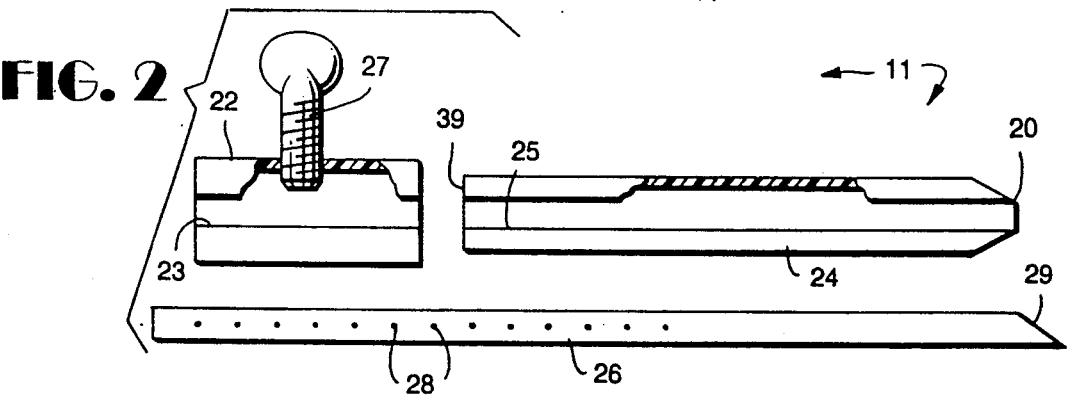
FIG. 2 is a side exploded view, partly in elevation and partly in cross-section, of the components associated with the first skull engaging point member of the stereotactic neurological instrument placement guide of FIG. 1.

FIG. 2 illustrates the first point member 11 as a slotted sleeve 22 which is rigidly attached to the arm 14, with the slot 23 therein preferably on the opposite face of the sleeve 22 as the arm 14. Disposed within the sleeve 22 is the slotted tubular element 24, having a slot 25 in one face thereof along the length thereof, both the slots 23 and 25 having a width which is great enough so that a catheter 26, or other neurological instrument, may be removed therethrough. Also, the internal diameter of the tubular element 24 is such that it provides a relatively tight fit for the catheter 26, but so that the catheter can move longitudinally therethrough. If the arm 14 is made of metal, it is desirable to make the slotted sleeve of a similar metal, while it is desirable to make the tubular member 24 of nylon, or a similar relatively rigid, durable plastic with lubricity characteristics.

The position of the tubular element 24 within the slotted sleeve 22 can be fixed by tightening the thumbscrew 27 which passes through the side wall of the sleeve 22, perpendicular to the dimension of elongation of the interior passageway, and the slot 23, therein. End termination 20 of the tubular element 24 actually engages a burr hole in the skull, and is preferably shaped in a manner so as to stabilize the first point member within the burr hole. This can be accomplished, as illustrated in FIGS. 1 and 2, by forming the termination 20 as a truncated cone.

Note that the catheter 26 preferably has indicia 28 formed along the length thereof. The position of those indicia with respect to a fixed point on the device 10 (typically on the tubular element 24) can be used as a guide by the neurosurgeon for insertion of the catheter 26 to make sure that it has been inserted to the proper position, i.e. so that the lead tip 29 thereof is at the target location in the brain ventricle or other target area.

Figure 3:
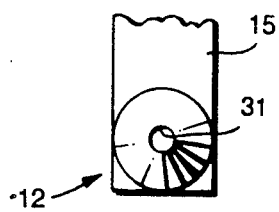
FIG. 3 is an end view of a second embodiment of the second skull engaging point member of the stereotactic neurological instrument placement guide of FIG. 1.

It is preferred that the second skull engaging point member 12 merely comprise a conical element terminating in a tip 30, which is integral with or rigidly affixed to the arm 15. However, under some circumstances it may be desirable to form the termination of the second point member 12 so that it can surround a nipple marker, to facilitate accurate placement. Such a second skull engaging point member is shown generally by reference numeral 12' in FIG. 3, the member 12' being formed as a hollow truncated cone, with means defining an interior surface 31 which is circular and has a diameter approximately equal to the outside diameter of nipple marker 32 (see FIG. 4).

Figure 4:
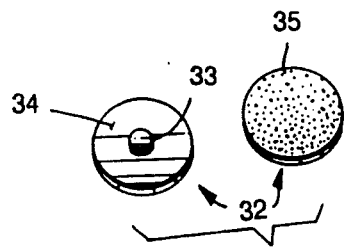
FIG. 4 illustrates a pair of nipple markers that may be utilized in the practice of the method of the invention, one shown in top perspective and the other in bottom perspective.

FIG. 4 illustrates conventional nipple markers that may be utilized with the device 10 to ensure proper positioning thereof in the surgical procedures according to the invention. The conventional nipple markers 32 are discs of plastic, or like material that is not clearly visible in a CT, MRI, or other imaging procedure, with a small cylinder of lead (or like radiopaque material) 33, having a diameter of about one-two millimeters, on the top face 34, concentric therewith. The top face 34 is smooth and uncoated, while the bottom face 35 has adhesive affixed thereto (it may have a release paper covering). In use, when a nipple marker 32 is in place, a scribe mark on the skull can be provided by passing a trocar or screw around disc Alternatively, an entire nipple marker 32 may be used for placement, for example with respect to the second point member 12' of FIG. 3.

FIG. 5 illustrates utilization of the device 10 in the placement of a ventricular drain or shunt. Nipple markers 32 are placed where a burr hole 37 is to be formed in the patient's skull at a location determined to be acceptable for the particular patient and procedure involved by the neurosurgeon, and at a fixing point 38 on the opposite side of the patient's skull from the burr hole 37. The manner in which the fixing point 38 is precisely located will be described hereafter.

The neurosurgeon moves the first arm 14 so that it is widely spaced from the second arm 15, and then moves the second point member 12 into operative contact with the fixing point 38. Then the arm 14 is moved toward the arm 15, with the members 11, 12 moving along a common linear axis 13, until the termination 20 of the member 11 is stabilized within the burr hole 37. During this initial phase, the position of the arm 14 with respect to the arm 15 may be fixed, and the tubular element 24 may slide with respect to the slotted sleeve 22, or vice versa.

Once the termination 20 has properly stabilized within the burr hole 37, either the thumbscrew 18 can be tightened to lock the relative positions of the arms 14, 15 in place (with the thumbscrew 27 likewise tightened), or the elastic band 19 can be placed around the arms 14, 15 to bias them together. When the device 10 is in this position, it is necessary to be sure that the slots 23, 25 are misaligned with each other so that when the catheter 26 is passed therethrough it cannot move sidewardly out of the guide provided by the slotted sleeve 22 and tubular element 24.

With the device 10 thus so positioned, the neurosurgeon then moves the catheter 26 into the guide provided by the sleeve 22 and element 24, inserting it into the skull until the appropriate indicia 28 is reached (e.g. at the top surface 39 of the element 24) indicating that the catheter 26 has been inserted a distance calculated to be the distance of the ventricle area to be drained from the burr hole 37.

Once the catheter 26 has been thus properly positioned it is desirable to be able to remove the device 10 from operative engagement with the patient's head, and the catheter 26. This is accomplished by loosening the thumbscrew 27, then rotating the tubular member 24 so that the slot 25 therein is aligned with the slot 23 in the sleeve 22, the slots 23, 25 providing a channel which is open, and then—with the termination point 20 pulled away from the burr hole 37 (either by moving the tubular element 24, or by moving the entire arm 14)—moving the device 10 in the direction of the guide element 17 (that is away from the patient's head) so that the catheter passes through the channel defined by the slots 23, 25. Thus the catheter 26 remains in place while the device 10 is completely detached.

It is to be understood that a wide variety of modifications may be made in the stereotactic placement guide 10. For example, the tubular element 24 could be continuous, rather than slotted, and it could be removed from engagement with the catheter 26 by pulling it out over the top of the catheter 26, along the length thereof, and then the catheter 26 moved out through the slot 23. Also the sleeve 22 could be pivotally connected to the arm 14, or detachably connected thereto, and a wide variety of other modifications are also possible.

Figure 8:
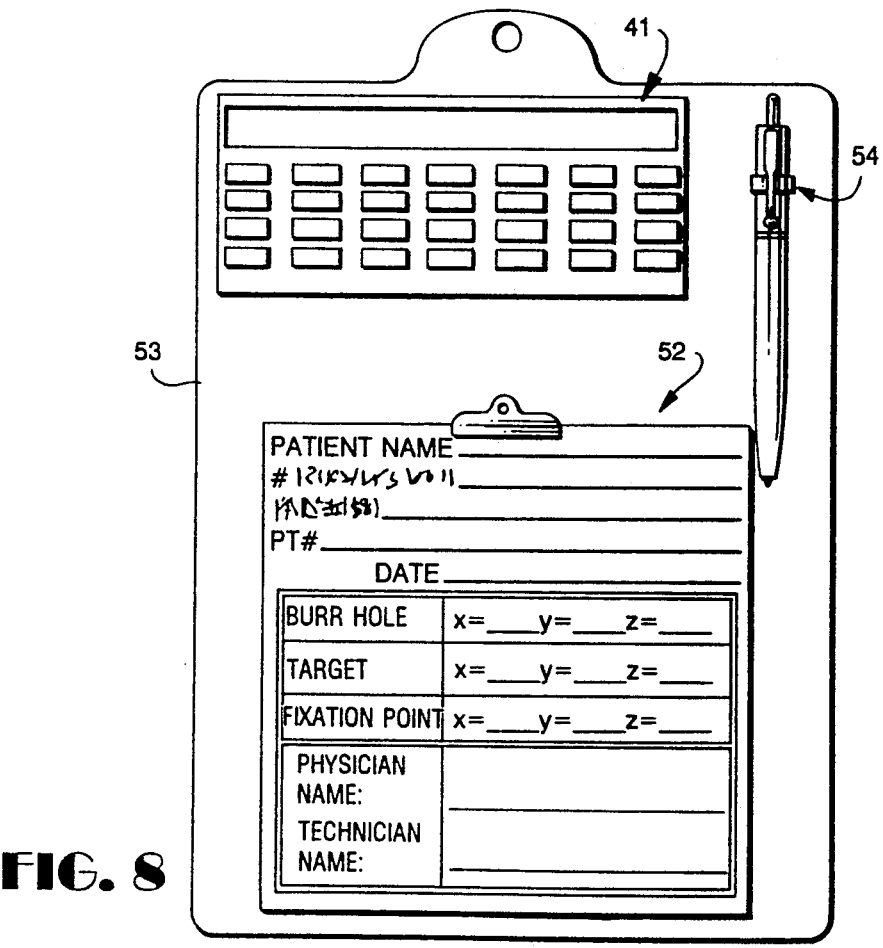
FIG. 8 is a top plan view of a programmable calculator and record keeping pad mounted in a manner facilitating its utilization in a practice of the method according to the invention.

According to the present invention, it is necessary to accurately position the fixing point 38, otherwise the goals of accurate placement of the neurological instrument (e.g. catheter 26) will not be achieved. Accurate placement of the nipple marker 32, or the like, at the fixing point 38 is accomplished utilizing conventional coordinate multiplanar tomographic imaging equipment, shown schematically generally by reference numeral 40 in FIG. 6, and by utilizing a programmable calculator 41 (see FIG. 8), or a like computer.

The coordinate multiplanar tomographic imaging equipment 40 preferably is CT or MRI equipment, but other coordinate multiplanar tomographic imaging techniques and equipment may also be utilized. Such equipment 40 typically cooperates with a table 42 on which the patient rests, and the equipment 40 is disposed at a tilt or gantry angle 43 with respect to table 42 to ensure proper imaging. A computer control 44 controls the equipment 40, and desired information is viewable on the screen 45. During the imaging operation, the table 42 is incrementally advanced in the Z dimension illustrated in FIG. 6.

Figure 6:
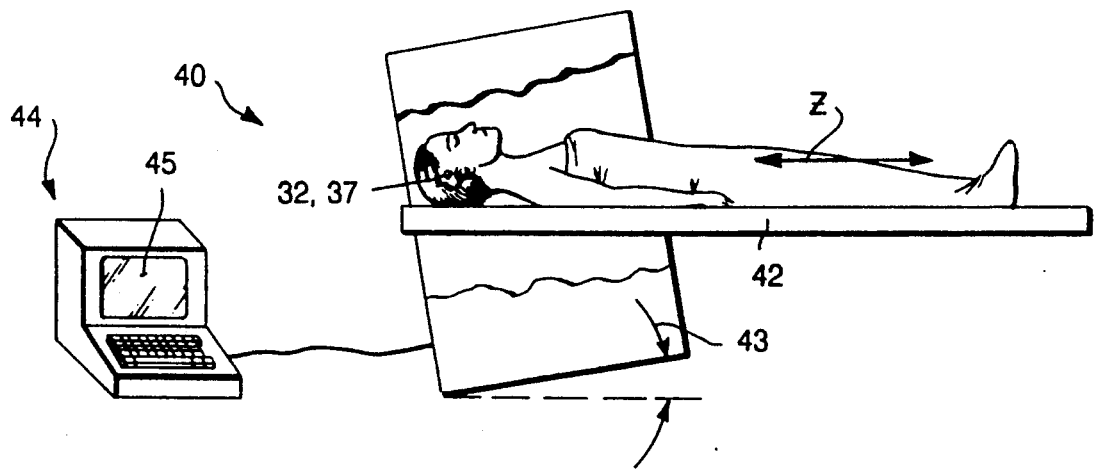
FIG. 6 is a schematic view of conventional coordinate multiplanar tomographic imaging equipment utilized in the practice of the method according to the invention.

When the patient is placed in the equipment 40, a nipple marker 32 or the like for the burr hole 37 is in place (being shown in an exaggerated size in FIG. 6). Utilizing the equipment 40, the operator determines the X, Y, and Z (Z being the position along the table 42) coordinates of that location, which is a first point. The equipment 40 operator will have already been instructed by the neurosurgeon as to what the target location in the brain has been decided upon. For example the target location may be a particular second point 47 (see FIG. 7, a representation of an image of the patient's skull on the screen 45 at one particular slice) within the ventricle 48. The coordinates of the second point 47 are also determined by the operator as is conventional.

The operator operates the equipment 40 to conduct a conventional imaging operation, e.g. CT scan. On the screen 45 all of the data associated with each slice of the imaging operation is recorded, including the position along the table 42 (the dimension Z) and the table moves an increment between each slice, the increment typically being about 5 to 10 millimeters.

Figure 7:
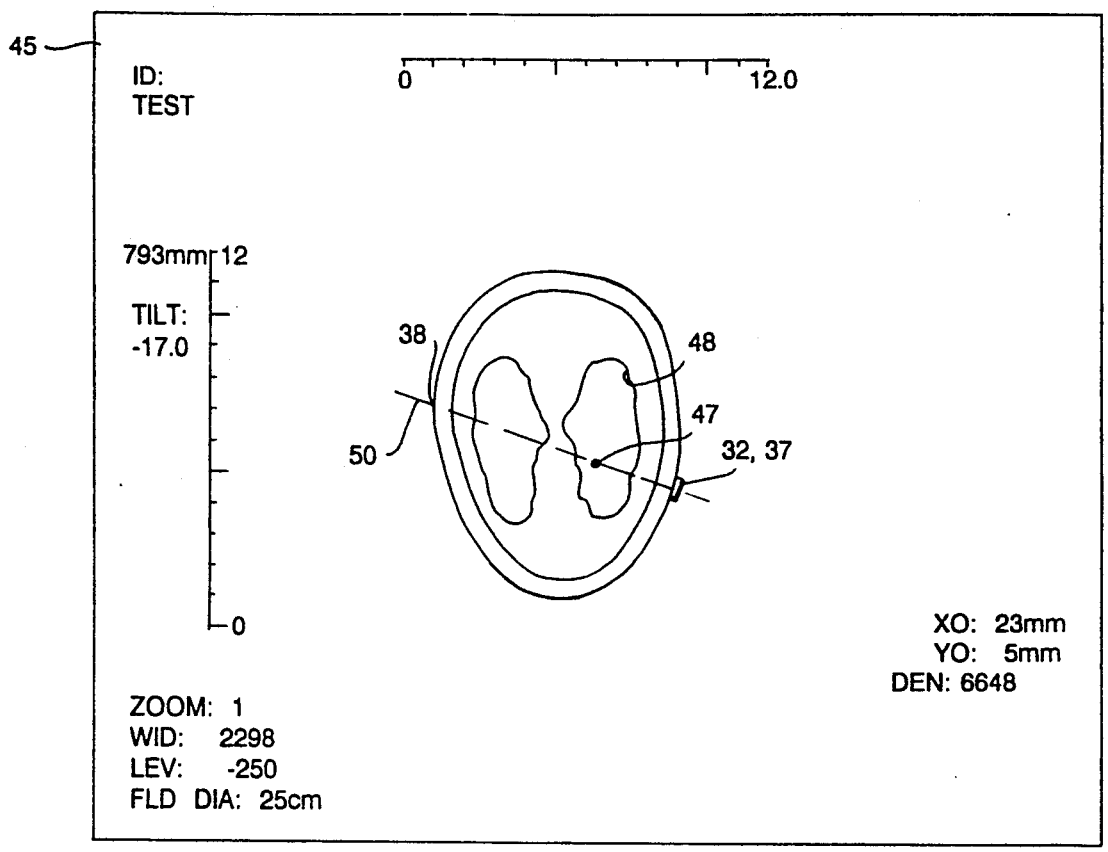
FIG. 7 is a schematic view of a screen of the apparatus of FIG. 6 at one of the slice locations.

Utilizing the coordinates of the first point 32, 37 and the second point 47 (the X, Y and Z coordinates of each), the angle of inclination 43 of the scanning equipment 40 with respect to the table 42 (the gantry angle), and the incremental advancement (the incremental advance in dimension Z, typically 5 millimeters), the distance between the first and second points can be calculated, and the loci of points along a line containing the first and second points can be determined, the line being shown schematically at 50 in FIG. 7. This calculation is performed utilizing the programmable calculator 41 or like computer, utilizing vector parameterization. FIG. 7 illustrates the points 32, 47, 38 all on the same screen only for the purposes of facilitating the description of the invention. However, in a real life use no single screen ("slice") will contain all three points since they are not coplanar with the "slices".

Pursuant to vector parameterization, as is well known per se in vector mathematics, for any line passing through a volume a vector parameterization for the line can be derived utilizing the equation $r(t) = a + tb$ where t is real and r, a and b are nonzero vectors. Vector "a" passes from the origin of the coordinate system to a point on the line to be described. Vector b is on the line and gives the line direction. t is a scalar which ranges over the set of real numbers. Varying t varies the vector r(t), but the tip of r(t) remains on the line described. Given any two points in the cartesian coordinate system, a line through these two points can be described using the vector parameterization. The line can then be extended through space by changing the scalar value t.

A representation of the various program steps that will performed by the calculator 41 in calculating the desired data is provided by the following BASIC computer program:

```
10 INPUT "BURR HOLE TABLE POSITION", C
20 INPUT "BURR HOLE X VALUE", A
30 INPUT "BURR HOLE Y VALUE", B
40 INPUT "TARGET CT TABLE POSITION", Z
50 INPUT "TARGET X VALUE", X
60 INPUT "TARGET Y VALUE", Y
70 INPUT "CT TABLE INCREMENT", M
80 INPUT "CT GANTRY ANGLE (DEGREES)", L
90 N = M*COS(L)
100 E = C*SIN(L) + B
110 F = C*COS(L)
120 V = Z*SIN(L) + Y
130 W = Z*COS(L)
140 D = CINT( (X−A)² + (V−E)² + (W−F)² )^½
150 PRINT "BURR HOLE TO TARGET DISTANCE"
160 PRINT D; "MM"
170 P = W−(10*N)
180 FOR H=1 TO 20
190 K = (P−F)/(W−F)
200 Q = CINT (A+(X−A)*K)
210 R = E+(V−E)*K
220 S = F+(W−F)*K
230 U = CINT(S/COS(L))
240 T = CINT(R−U*SIN(L))
250 PRINT "TABLE POSITION=";U;",";"X=";Q;",";"Y=";T
260 P = P+N
270 NEXT H
280 STOP
```

Line 10 is the input for the burr hole Z coordinate, line 20 for the burr hole X coordinate, and line 30 for the burr hole Y coordinate. Line 40 is for the target (second point 47) Z coordinate, line 50 for the target X coordinate, and line 60 for the target Y coordinate. The calculation in line 90 thus converts the CT table increments in the original coordinate system to Z-axis movement increments in a new coordinate system. Calculation 100 converts the burr hole Y value to the new coordinate system, and line 20 converts the burr hole Z value. Calculation 120 converts the Y value of the target to the new coordinate system, and calculation 130 the Z target value. Calculation 140 is the distance of the burr hole (37) to the target (47), with the function "CINT" being a round off function ("cut integer"), which is preferably employed. This distance is printed out at 150.

Calculation 170 is the calculation of the Z value 10 incremental movements from the target Z value in the new coordinate system. The instruction on line 180 initiates the loop in the computer program. Calculation 190 determines the conversion factor for a point on a vector in three D space, calculation 200 determines the new X value for a parallel plane −10+0+10 incremental movements from the plane containing the target point (47). Calculation 210 is the new Y value for the above-mentioned parallel plane, while 220 is the calculation for the new Z value for the above-mentioned parallel plane. In calculation 230 the new Y value is converted to the original coordinate system, while calculation 240 converts the new Z value to the original coordinate system. Calculation 260 determines the new parallel plane Z value one incremental movement in the new coordinate system. Line 270 is the closing loop statement, and after H 1 to 20 has been run, 280 provides the end of program.

In the original coordinate system. An exemplary printout provided once all of the H values have been run (step 250 is completed for H 1 to 20), and the CT scan is complete, is as follows (this provides the loci of points on the calculated coordinate line):

```
71 MM
TABLE POSITION = 150 ,X= 50 ,Y=45
TABLE POSITION = 145 ,X= 48 ,Y=43
TABLE POSITION = 140 ,X= 45 ,Y=40
TABLE POSITION = 135 ,X= 43 ,Y=38
TABLE POSITION = 130 ,X= 40 ,Y=35
TABLE POSITION = 125 ,X= 37 ,Y=32
TABLE POSITION = 120 ,X= 35 ,Y=30
TABLE POSITION = 115 ,X= 33 ,Y=27
TABLE POSITION = 110 ,X= 30 ,Y=25
TABLE POSITION = 105 ,X= 27 ,Y=22
TABLE POSITION = 100 ,X= 25 ,Y=20
TABLE POSITION =  95 ,X= 22 ,Y= 17
TABLE POSITION =  90 ,X= 20 ,Y= 15
TABLE POSITION =  85 ,X= 17 ,Y= 12
TABLE POSITION =  80 ,X= 15 ,Y= 10
TABLE POSITION =  75 ,X= 12 ,Y=  7
TABLE POSITION =  70 ,X= 10 ,Y=  5
TABLE POSITION =  65 ,X= 7  ,Y=  2
TABLE POSITION =  60 ,X= 5  ,Y=  0
TABLE POSITION =  55 ,X= 2  ,Y= −3
Break in 280
Ok
```

The printout provided above may be accomplished utilizing a stand alone printer connected to the calculator 41, or by a printer associated with the calculator 41.

Utilizing the printout of table positions as provided above, the operator of the equipment 40, 41, can determine the most likely position for the third point 38. Then, with the patient still in the scanner (not having been removed from the equipment 40), the operator can return the table 42 to the desired position, train on a laser light which shows a line on the skull, then put on a nipple marker 32 at fixing point 38, and repeat the slice at that table position. Only if the new slice indicates misalignment of the fixing point 38 need the nipple marker 32 be repositioned.

The data obtained from running the equipment 40, 41 for a particular patient is preferably recorded, such as by utilizing the pad 52 mounted on the board 53 with the programmable calculator 41, to keep with the patient's file. A writing implement 54 may also be mounted on the board 53, providing an effective tool for facilitating the procedures according to the invention.

While the exemplary methods according to the invention have been described above with particular reference to a ventriculostomy procedure for a human patient, it is to be understood that the procedures are applicable to other neurological methods, such as biopsy, radioactive seed placement, and lesion generation. In general, according to the present invention a neurological instrument placement procedure for a human patient, utilizing an instrument guide having opposed point members disposed on a common linear axis, is provided, comprising the steps of substantially sequentially: (a) Marking the proposed position of a burr hole on the patient's skull. (b) Deciding upon the location of a target point within the patient's skull. (c) Effecting coordinate multiplanar tomographic imaging (e.g. CT, MRI, etc.) of the patient's skull and brain. (d) Utilizing data from step (c), calculating a coordinate line between the burr hole proposed position and the target point. (e) Utilizing the calculated coordinate line, determining a fixing point on the patient's skull opposite the proposed position of the burr hole, and marking that fixing point on the patient's skull. (f) Forming a burr hole in the patient's skull at the marked proposed burr hole position. (g) Placing the instrument guide into operative association with the patient's skull so that the opposed point members engage the burr hole and the fixing point. (h) Passing a neurological instrument into the burr hole, positively guided by the instrument guide, along the common linear axis of the opposed point members, until the instrument reaches the target point. And, (i) performing a neurological procedure with the neurological instrument at the target point.

The vector parameterization described above, according to the invention, is applicable to other medical procedures besides neurological procedures. The vector parameterization according to the invention is utilizable in general for determining the position of a line (typically a straight line) between two points on or within a human patient's body utilizing data normally determined from a coordinate multiplanar tomographic imaging of the patient's body during which the patient is disposed at a non-zer angle and while there is an incremental advance between images. Such a method comprises the following steps: (a) During coordinate multiplanar tomographic imaging of the patient's body, determining the coordinates of a first point on or within the patient's body. (b) During coordinate multiplanar tomographic imaging of the patient's body, determining the coordinates of a second point on or within the patient's body. (c) Determining the non-zero angle of inclination of the patient and the incremental advance between images. And, (d) utilizing the coordinates of the first and second points, the non-zero angle of inclination, and the incremental advance, by vector parameterization calculating the distance between the first and the second points and the loci of points along a line containing the first and second points.

In order to improve the utility of the stereotactic neurological instrument placement guide illustrated in FIGS. 1 through 5, and described above, the cerebral instrument guide frame 56, illustrated in FIGS. 9 through 12, is provided, as well as a computer program associated therewith.

The cerebral instrument guide frame 56 comprises the first frame member 57 and a second frame member 58. Preferably both frame members 57, 58 are arcuate, e.g. hemi-circular or semicircular, having a radius, with the radius of the second arcuate member 58 greater than that of the first arcuate member 57. The member 57 has first and second ends 59, 60 respectively, while the member 58 has first and second ends 61, 62 respectively. These ends 59-62 have aligned openings 63-66, respectively, therein, the openings 63-66 defining a common axis 67.

Figure 10:
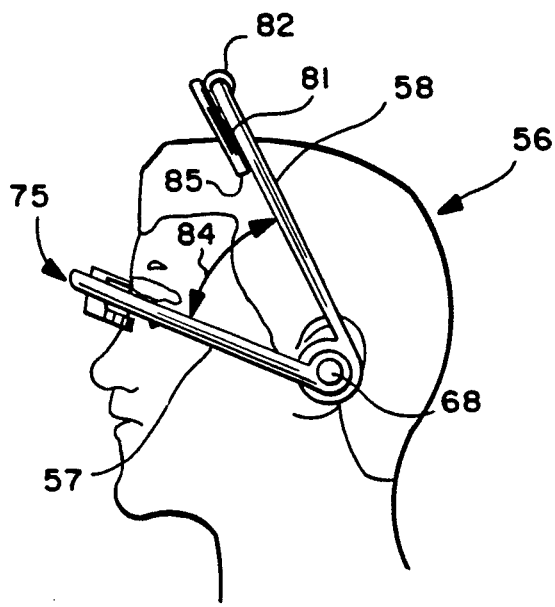
FIG. 10 is a side view of a patient's head with the cerebral instrument guide frame of FIG. 9 shown in operative association therewith to mark a burr hole site.
Figure 11:
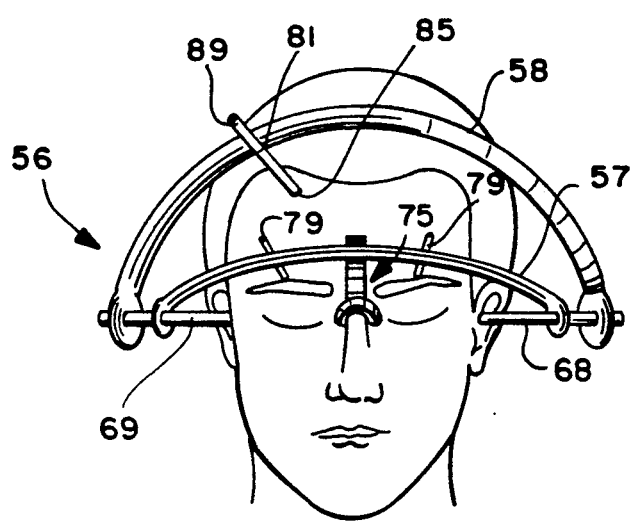
FIG. 11 is a front view like that of FIG. 10.
Figure 12:
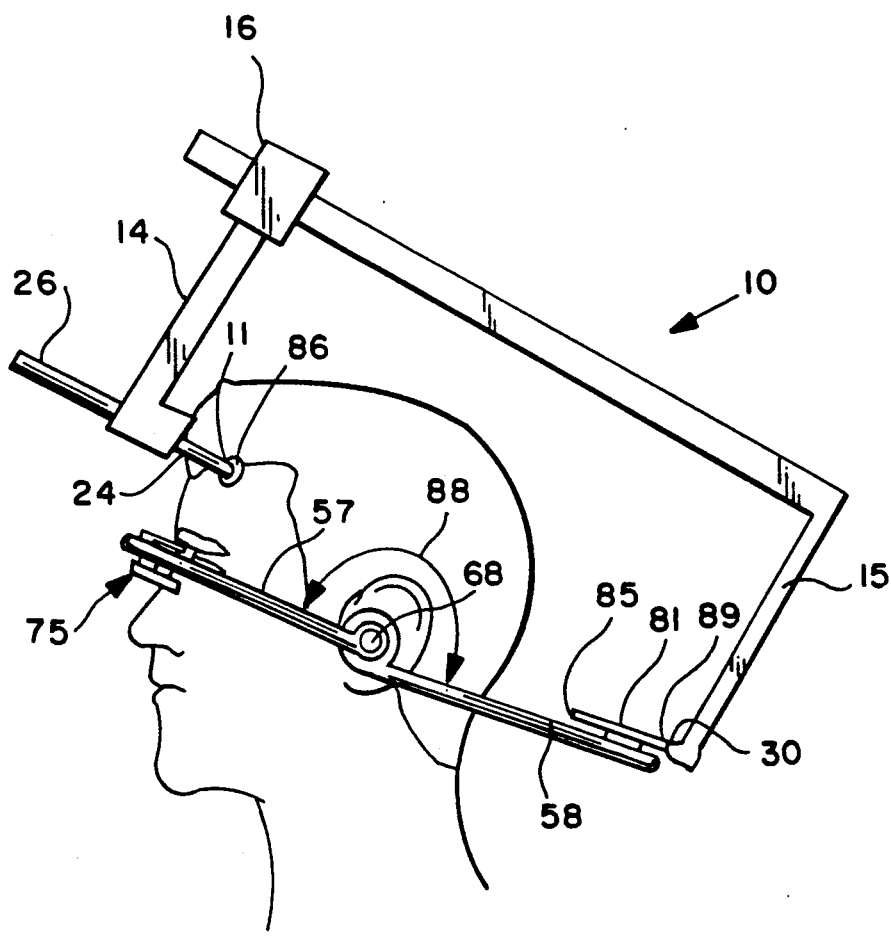
FIG. 12 is a view like that of FIG. 10 only showing the stereotactic neurlogical instrument placement guide of FIG. 1 mounted in association with the cerebral instrument guide frame and the burr hole site on the patient's skull, for insertion of a catheter.

Mounted within the openings 63, 65 is a first rigid ear fixator rod 68, and mounted within the openings 64, 66 is a second such rod 69. The rods 68, 69 preferably have soft material, indicated by the soft rubber coverings 70, 71, covering the inner ends thereof which are adapted to engage and seat into the external auditory meati of a human patient's head, as illustrated in FIGS. 10 through 12. The rods 68, 69 are slidable along the axis 67 to accommodate patient's having different head sizes, and also to ensure positive seating in the patient's ears. The sliding action may be achieved merely by providing a friction fit between the openings 63-66 and rods 68, 69, or—as illustrated in FIG. 9 in order to ensure that the relative positions of the members 57, 58 do not move with respect to each other—by providing collars 72, 73 that are attached to the ends 59-62 so as to not be linearly movable with respect thereto while allowing pivotal rotation, utilizing any suitable conventional means (such as stops applied to the collars 72, 73 on opposite sides of the ends 59-62 after proper location thereof with respect to the collars 72, 73), with the rods 68, 69 received within the collars 72, 73 and having a friction fit therewith so that they are movable along the axis 67, but will remain in place in any position to which they have been moved.

Mounted on the first arcuate member 57 is the adjustable nasal bridge fixation element shown generally by reference numeral 75. The element 75 includes a curved inner end termination 76 adapted to engage the bridge of a person's nose, as illustrated in FIGS. 10 through 12, and a shaft 77 which extends radially with respect to the arcuate element 57. The radial position of the curved end portion 76 may be adjusted by providing the shaft 77 with a friction fit with respect to a sleeve 78 (see FIG. 9) rigidly fixed to the element 57.

Figure 9:
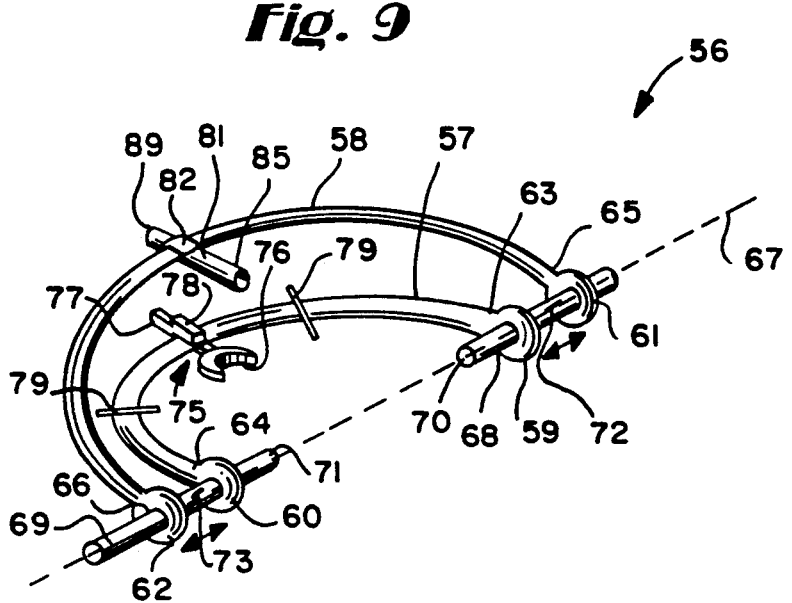
FIG. 9 is a top perspective view of an exemplary cerebral instrument guide frame according to the present invention.

Also, the element 57 preferably has orbit pads 79 mounted thereon, on opposite sides of the nasal bridge fixation element 75, for engaging the patient's orbits, these pads being shown by reference numeral 79 in FIGS. 9 and 11. The elements 79 also extend radially with respect to the arcuate element 57, and preferably pass through radial openings in the element 57, having a friction fit therewith.

The frame 56 also includes, mounted on the second arcuate member 58, an instrument guide 81, which is a substantially tubular element which is directed to the mid point of the common axis 67. The internal diameter or cross-sectional area of the tubular element 81 is great enough to receive a needle which is used for marking the burr hole site on a patient's skull. Preferably the position of the element 81 on the second arcuate member 58 is adjustable along the arc, although the element 81 always is directed to the mid point of the axis 67 regardless of its position with respect to the element 58. It is movably positioned with respect to the element 58, for example, by rigid attachment thereof to a collar 82 (see FIG. 10) which makes a friction fit with the element 58 (having the same arcuate radius thereof; the collar 82 may also be keyed to element 58).

In the utilization of the device 56 in a method of positively locating the burr hole site on a patient's skull during a neurological procedure on a human patient, it is desirable to calculate, with a computer, the angular positions of the frame elements 57, 58 with respect to each other in order to properly mark the burr hole site. A computer program is utilized for this purpose. The program accepts data from computed tomographic images, represented as points in space, the following: a target point in a cerebral ventricle, a point representing the intended burr hole site on the skull, a point at the right external auditory meatus, a point at the left external auditory meatus, and a point representing the interior superior edge of either bony orbit. The program corrects for CT scanner non-zero gantry angle, and then calculates an angle at which to separate the arcs 57, 58, this angle being shown by reference numeral 84 in FIG. 10. The program also calculates an angle between a line containing the mid point of the axis 67 and the skull point, and the axis 67. The sliding guide 81 on the arcuate member 58 is then set at the second calculated angle, and thus the sliding guide 81 is directed at the point on the skull—at the end 85 of the element 81—where the burr hole site will be marked by passing a needle through the tubular guide 81.

In order to determine the correct angulation in degrees between the arcuate elements 57, 58 of the frame 56 for marking the skull burr hole position, and optionally for accepting the fixing point of the element of FIG. 1, the following computer program may be utilized:

```
10 INPUT "TARGET TABLE POSITION", C
20 INPUT "TARGET X VALUE", A
30 INPUT "TARGET Y VALUE", B
40 INPUT "BURR HOLE TABLE POSITION", F
50 INPUT "BURR HOLE X VALUE", D
60 INPUT "BURR HOLE Y VALUE", E
70 INPUT "RT EAC TABLE POSITION", I
80 INPUT "RT EAC X VALUE", G
90 INPUT "RT EAC Y VALUE", H
100 INPUT "LT EAC TABLE POSITION", L
110 INPUT "LT EAC X VALUE", J
120 INPUT "LT EAC Y VALUE", K
130 INPUT "BROW TABLE POSITION", P
140 INPUT "BROW X VALUE", M
150 INPUT "BROW Y VALUE", N
160 INPUT "GANTRY ANGLE IN DEGREES", Q
170 O = Q*3.14159/180
180 R = C*SIN(O) + B
190 S = C*COS(O)
200 T = F*SIN(O) + E
210 U = F*COS(O)
220 V = I*SIN(O) + H
230 W = I*COS(O)
240 X = L*SIN(O) + K
250 Y = L*COS(O)
260 Z = P*SIN(O) + N
270 AA = P*COS(O)
280 LL = (G+J)/2
```

```
290 MM = (V+X)/2
300 NN = (W+Y)/2
310 BB =
(AA*X-AA*V+W*Z-W*X+Y*V-Y*Z)/(M*V-M*X+G*X-G*Z+J*Z-J*V)
320 CC =
(AA*J-AA*G+W*M-W*J+Y*G-Y*M)/(Z*G-Z*J+V*J-V*M+X*M-X*G)
330 DD =
(U*X-U*V+W*T-W*X+Y*V-Y*T)/(D*V-D*X+G*X-G*T+J*T-J*V)
340 EE =
(U*J-U*G+W*D-W*J+Y*G-Y*D)/(T*G-T*J+V*J-V*D+X*D-X*G)
350 FF = ((BB)^2+(CC)^2+(1))^.5
360 GG = ((DD)^2+(EE)^2+(1))^.5
370 HH = ((BB*DD)+(CC*EE)+(1))/(FF*GG)
380 II = (1-(HH)^2)^.5
390 JJ = ATN(II/HH)
400 KK = ABS(JJ)*180/3.14159
410 FA = CC*(Y-W)-1*(X-V)
420 FB = 1*(J-G)-BB*(Y-W)
430 FC = BB*(X-V)-CC*(J-G)
440 FD = ((BB*D)-(BB*LL)+(CC*T)-(CC*MM)+(1*U)-(1*NN))
450 FE = ((FA*D)-(FA*LL)+(FB*T)-(FB*MM)+
(FC*U)-(FC*NN))
460 IF (FD > 0) AND (FE > 0) THEN PRINT "ARC ANGLE
FOR BURR HOLE", CINT(KK)
470 IF (FD > 0) AND (FE < 0) THEN PRINT "ARC ANGLE
FOR BURR HOLE", CINT(-KK)+180
480 IF (FD < 0) AND (FE > 0) THEN PRINT "ARC ANGLE
FOR BURR HOLE", CINT(-KK)
490 IF (FD < 0) AND (FE < 0) THEN PRINT "ARC ANGLE
FOR BURR HOLE", CINT(KK)-180
500 IF (FD < 0) AND (FE = 0) THEN PRINT "ARC ANGLE
FOR BURR HOLE", "-90"
510 IF (FD > 0) AND (FE = 0) THEN PRINT "ARC ANGLE
FOR BURR HOLE", "90"
520 IF (FD = 0) AND (FE < 0) THEN PRINT "ARC ANGLE
FOR BURR HOLE", "-180"
530 IF (FD = 0) AND (FE > 0) THEN PRINT "ARC ANGLE
FOR BURR HOLE", "180"
```

```
540 OO = (J-G)*(D-LL)+(X-V)*(T-MM)+(Y-W)*(U-NN)
550 PP = (((G-J)^2+(V-X)^2+(W-Y)^2)^.5 *(((D-LL)
^2+(T-MM)^2+(U-NN)^2)^.5)
560 QQ = OO/PP
570 RR = (1-(QQ)^2)^.5
580 SS = ATN(RR/QQ)
590 TT = SS*180/3.14159
600 IF TT < 0 THEN TT = TT + 180
610 PRINT "SLIDE GUIDE ANGLE", CINT(TT)
620 UU = ((((A-D)^2+ (R-T)^2+(S-U)-2) *(200)^2-
((A-D)^2+(R-T)^2+(S-U)^2)*((D-LL)^2 +(T-MM)^
2+(U-NN)^
2)+((D-LL)*(A-D)+(T-MM)*(R-T)+(U-NN)*(S-U))
^2)^.5-((D-LL)*(A-D)
+(T-MM)*(R-T)+(U-NN)*(S-U)))/((A-D)
^2+(R-T)^2+(S-U)^2)
630 WWW = (D+(A-D)*UU)
640 XXX = (T+(R-T)*UU)
650 YYY = (U+(S-U)*UU)
660 VV = (-(((A-D)^2+ (R-T)^2+(S-U)^2)*(200)^
2-((A-D)^2+(R-T)^2+(S-U)^2)*((D-LL)^2+(T-MM)
^2+(U-NN)^
2)+((D-LL)*(A-D)+(T-MM)*(R-T)+(U-NN)*(S-U))
^2)^.5-((D-LL)*(A-D)+(T-MM)*(R-T)+(U-NN)*
(S-U)))/((A-D)^2+(R-T)^2+(S-U)^2)
670 WWWW = (D+(A-D)*VV)
680 XXXX = (T+(R-T)*VV)
690 YYYY = (U+(S-U)*VV)
700 IF D<A AND A<WWW THEN GOTO 750
710 IF D>A AND A>WWW THEN GOTO 750
720 IF D<A AND A<WWWW THEN GOTO 790
730 IF D>A AND A>WWWW THEN GOTO 790
740 IF D=A THEN GOTO 830
750 WW=WWW
760 XX=XXX
770 YY=YYY
780 GOTO 870
790 WW=WWWW
```

```
800 XX=XXXX
810 YY=YYYY
820 GOTO 870
830 IF T<R AND R<XXX THEN GOTO 750
840 IF T>R AND R>XXX THEN GOTO 750
850 IF T<R AND R<XXXX THEN GOTO 790
860 IF T>R AND R>XXXX THEN GOTO 790
870 ZZ = (YY*X-YY*V+W*XX-W*X+Y*V-Y*XX)/(WW*V-WW*X+
G*X-G*XX+J*XX-J*V)
880 AAA = (YY*J-YY*G+W*WW-W*J+Y*G-Y*WW)/(XX*G-XX
*J+V*J-V*WW+X*WW-X*G)
890 BBB = ((ZZ)^2+(AAA)^2+(1))^.5
900 CCC = ((BB*ZZ)+(CC*AAA)+(1))/(FF*BBB)
910 DDD = (1-(CCC)^2)^.5
920 EEE = ATN(DDD/CCC)
930 FFF = ABS(EEE)*180/3.14159
940 FG = ((BB*WW)-(BB*LL)+(CC*XX)-(CC*MM)+
(1*YY)-(1*NN))
950 FH = ((FA*WW)-(FA*LL)+(FB*XX)-(FB*MM)+
(FC*YY)-(FC*NN))
960 IF (FG > 0) AND (FH > 0) THEN PRINT "ARC ANGLE
FOR FIX POINT", CINT(FFF)
970 IF (FG > 0) AND (FH < 0) THEN PRINT "ARC ANGLE
FOR FIX POINT", CINT(-FFF)+180
980 IF (FG < 0) AND (FH > 0) THEN PRINT "ARC ANGLE
FOR FIX POINT", CINT(-FFF)
990 IF (FG < 0) AND (FH < 0) THEN PRINT "ARC ANGLE
FOR FIX POINT", CINT(FFF)-180
1000 IF (FG < 0) AND (FH = 0) THEN PRINT "ARC ANGLE
FOR FIX POINT", "-90"
1010 IF (FG > 0) AND (FH = 0) THEN PRINT "ARC ANGLE
FOR FIX POINT", "90"
1020 IF (FG = 0) AND (FH < 0) THEN PRINT "ARC ANGLE
FOR FIX POINT", "-180"
1030 IF (FG = 0) AND (FH > 0) THEN PRINT "ARC ANGLE
FOR FIX POINT", "180"
1040 GGG = (J-G)*(WW-LL)+(X-V)*(XX-MM)+(Y-W)*(YY-NN)
1050 HHH = (((G-J)^2+ (V-X)^2+(W-Y)^2)
```

```
^.5)*(((WW-LL)^2+(XX-MM)^2+(YY-NN)^2)^.5)
1060 III = GGG/HHH
1070 JJJ = (1-(III)^2)^.5
1080 KKK = ATN(JJJ/III)
1090 LLL = KKK*180/3.14159
1100 IF LLL < 0 THEN LLL = LLL + 180
1110 PRINT "SLIDE ANGLE FOR FIX POINT", CINT(LLL)
```

The program as set forth above has the following functional aspect:
10-160 Data (X,Y,Z) Entry
170-270 Gantry Tilt Correction of Data
280-300 Midpoint (Between EAC Points, Along Axis 67) Determination
310-340 Derivation of Vectors Describing Plane Through Fixed Arc and Plane Through EAC's and Burr Hole
350-400 Derivation of Angle Between Two Planes Above
410-450 Cross Product of Midpoint to Burr Hole Vector and EAC to EAC Vector
460-530 Spacial Conditions to be Satisfied to Determine Correct Slide (81, 82) Guide Angle
540-610 Determination of Slide Guide Angle
620-690 Determination of Intercepts of Line Through Target and Burr Hole with Sphere Created by Free Arc Rotation
700-860 Variable Conditions Applied to Determine Correct Intercept
870-1030 Derivation of Angle Between Fixed and Free Arcs for Acceptance of Stereotactic Instrument Placement Guide (10, FIG. 1) Fixing Point 30 (Similar to 310-530)
1030-1110 Derivation of Slide Guide Angle for Accepting Fixed Point 30 of Stereotactic Instrument Placement Guide (10, FIG. 1) (Similar to 540-610)

As can be seen from the computer program, it utilizes, in part, vector parameterization, to correct for any non-zero angle of inclination between imaging equipment and the patient while there is an incremental advance between images. Thus the gantry angle 43 is taken into account.

In a method of positively locating a burr hole site on a patient's skull during a neurological procedure utilizing the guide frame 56, the following steps are practiced:

(a) Coordinate multi-planar tomographic imaging (e.g. a CT scan) is effected of the patient's head, as schematically illustrated in FIG. 6.

(b) During the practice of step (a) locations of the target in the patient's head, the burr site on the patient's skull, the patient's left and right auditory medati, and at least one of the patient's orbital ridges, are determined.

(c) With the computer 44 or 41, the data determined in step (b) is used to calculate the angular positions (the angle 84) of the frame members 57, 58 to correctly mark the burr hole site on the patient's skull.

(d) Then the ear fixations (that is rods 68, 69) are moved into positive contact with the patient's ears (auditory medati), and the nasal bridge fixation 75 is moved into positive contact with the patient's nasal bridge.

(e) The second frame 58 of the guide frame 56 is then moved with respect to the first member 57 to the proper angular orientation 84 to mark the burr hole site, and moving the instrument guide 81 is moved to the proper position along the second frame member 58, and the burr hole site is marked using the instrument guide 81 (as by passing a needle therethrough into contact with the patient's skull). Exemplary positions for marking the burr hole site utilizing the frame 56 are illustrated in FIG. 10, the burr hole site—when marked—being provided at 86 as illustrated in FIG. 12.

After practicing the above steps, the frame 56 may be removed from the patient's skull, and the program first described with respect to the calculator 41 utilized to determine the fixing point. Alternatively, the method described above with respect to the frame 56 may be utilized for positively locating the fixing point by the further step of (f) moving the second frame member 58 with respect to the first frame member 57 to have the proper angle 88 (see FIG. 12), typically about 160°-180°, for the fixing point on the patient's skull, and then marking the fixing point using the instrument guide 81.

As yet another alternative, the element 10 from FIG. 1, as illustrated in FIG. 12, may be mounted directly with the frame 56 after the burr hole is formed at the burr hole site 86, as by bringing the point 30 into contact with the end 89 of the instrument guide 81 opposite the inner end 85 thereof, while the skull engaging point member 11 is stabilized in the burr hole at the burr hole site 86. Thus in this embodiment, the element 81 itself provides the fixing point. The catheter 26 may then be passed through the element 24 as described earlier with respect to FIG. 5. Of course as also described earlier, instead of a catheter 26 another type of instrument may be utilized, passed to the target within the patient's skull (e.g. within one of the ventricles).

The device 10 may be used without the frame 56, as illustrated in FIG. 5, or with the frame 56, as illustrated in FIG. 12, depending upon what is best for a particular situation, and the location of the burr hole and fixing point sites may be practiced using both the procedure described above with respect to FIGS. 5 through 7 and the procedure described with respect to FIGS. 10 through 12, or just one of these procedures.

Thus according to the invention a simplified method of performing a neurological procedure on a human patient utilizing a scanner, a cerebral instrument guide frame, and an operating room, is provided. According to the invention it is not necessary to effect a second scan. Rather, the invention comprises the steps of substantially sequentially:

(a) Effecting coordinate multiplanar tomographic imaging (e.g. a CT scan) of the patient's head with the scanner while the patient's head is free of frame attachments (see FIG. 6), to obtain data necessary for performing a neurological procedure.

(b) Moving the patient to the operating room.

(c) In the operating room, utilizing the data from step (a), fixing the cerebral instrument guide frame (e.g. 56) on the patient's head (see FIGS. 10-12).

And, (d) substantially immediately after step (c), in the operating room, without transporting the patient back to the scanner 40 to effect a second imaging, performing the neurological procedure on the patient, utilizing the cerebral instrument guide frame 56 to guide one or more medical instruments (e.g. a catheter 26, light pipe, laser, etc.).

It is to be understood that the apparatus and procedures according to the present invention are to be interpreted broadly in conformance with the following claims, so as to encompass all equivalent procedures and devices.

What is claimed is:

1. A cerebral instrument guide frame for use with a live human patient, comprising:
a first arcuate member having first and second ends, and a radius;
a second arcuate member having first and second ends and a radius;
the radius of said second arcuate member greater than the radius of said first arcuate member;
aligned first and second openings provided adjacent each of said first and second ends of each of said first and second arcuate members;
first and second rigid ear fixator rods mounted in said aligned openings, the first in the openings adjacent said first ends of said first and second arcuate members, and the second in the openings adjacent said second ends of said first and second arcuate members, said rods mounted for movement with respect to said first and second arcuate members along a common axis passing through said openings, and said arcuate members mounted for pivotal movement with respect to each other about said common axis;
an abutment mounted on one of said arcuate members for engaging a portion of a patient's head to preclude movement of said arcuate member past that portion of the patient's head; and
an instrument guide mounted on the other of said arcuate members for guiding an instrument aligned therewith into contact with the patient's head, said guide directed to the midpoint of said common axis.

2. A frame as recited in claim 1 wherein said abutment comprises a nasal bridge fixation element, for engaging the bridge of a patient's nose.

3. A frame as recited in claim 2 wherein said instrument guide comprises a tubular element mounted to one of said arcuate elements for movement with respect to said element along the arcuate extent thereof.

4. A frame as recited in claim 2 wherein said abutment is mounted on said first arcuate element, and said instrument guide on said second arcuate element.

5. A frame as recited in claim 4 further comprising a pair of orbit pads mounted on said first arcuate element on opposite sides of said nasal bridge fixation element for engaging the patient's orbits.

6. A frame as recited in claim 3 wherein said tubular instrument guide element has an internal diameter slightly greater than the external diameter of a needle.

7. A frame as recited in claim 4 in combination with a stereotactic neurological instrument placement guide comprising:
skull engaging elements consisting of first and second skull engaging point members having a common central axis;
a lightweight frame mounting said skull engaging point members for controlled movement with respect to each other along said central axis;
means defining a linear guide passage in said first point member, a straight line extension of said linear guide passage extending along said common central axis, said linear guide passage being large enough for the passage of a neurological instrument therethrough; and
one of said point members of said skull engaging elements of said stereotactic neurological instrument guide engaging said tubular instrument guide element, and in alignment therewith.

8. A frame and guide combination as recited in claim 7 wherein said second point member comprises said one of said point members, wherein said first and second arcuate members make an angle of about 160-180 degrees with respect to each other with said second point member in alignment with said tubular instrument guide element, which is in contact with a fixing point on a patient's skull.

9. A frame as recited in claim 1 wherein each of said first and second arcuate members comprises a hemicircle.

10. A frame as recited in claim 4 wherein said nasal bridge fixation element is mounted for radial movement with respect to said first arcuate element, and said rods have soft material coverings at the actual ear engagement surfaces thereof.

11. A cerebral instrument guide for use with a live human patient' comprising:
- a first frame element having first and second ends, and a central portion;
- a nasal bridge fixation mounted on said first frame element at said central portion, and movable with respect to said first frame element;
- a second frame element having first and second ends, and a central portion;
- pivot means for mounting said first and second frame elements for pivotal movement with respect to each other about a common axis;
- an instrument guide mounted on said second frame element, and movable with respect thereto and directed toward the midpoint of said common axis; and
- means for positively locating said pivot means with respect to the patient's head so that said axis remains stationary with respect to a predetermined portion of the patient's head.

12. A guide as recited in claim 11 wherein said pivot means and said positively locating means comprise first and second rigid ear fixation rods adapted to be inserted into the patient's ears.

13. A guide as recited in claim 12 wherein said first and second rods are received within aligned openings in said first and second ends, respectively, of both said first and second frame elements, and said rods are slidable with respect to said frame elements to move toward and away from the patient's ears.

14. A guide as recited in claim 12 wherein said rods have soft material coverings at the actual ear engagement surfaces thereof.

15. A guide as recited in claim 11 wherein said first and second frame elements comprise first and second hemicircles, said second frame element hemicircle having a larger radius than said first element hemicircle.

* * * * *